United States Patent [19]

Maulding

[11] 4,297,353

[45] Oct. 27, 1981

[54] NON-IRRITATING INJECTABLE DOSAGE FORMS

[75] Inventor: Hawkins V. Maulding, Mendham, N.J.

[73] Assignee: Sandoz, Inc., E. Hanover, N.J.

[21] Appl. No.: 174,817

[22] Filed: Aug. 4, 1980

[51] Int. Cl.$^3$ .................... A61K 31/23; A61K 31/54; A61K 47/00

[52] U.S. Cl. .................................. 424/247; 424/312; 424/365

[58] Field of Search ...................... 424/247, 312, 365

[56] References Cited

U.S. PATENT DOCUMENTS 3,194,733  7/1965  Yale et al. ........................... 424/365

OTHER PUBLICATIONS

Chem. Abst. 77-79519x (1972).
Physician's Desk Reference, 28th Ed. (1974), pp. 1352–1354, 1380–1382 & 1384–1387.

Primary Examiner—Stanley J. Friedman
Attorney, Agent, or Firm—Gerald D. Sharkin; Robert S. Honor; Walter F. Jewell

[57] ABSTRACT

A non-irritating injectable dosage form of a tissue irritating medicament, comprising the medicament and a pharmaceutically acceptable glyceride vehicle comprising a glycerol ester of a saturated or unsaturated fatty acid having from 6 to 20 carbon atoms or mixtures thereof.

10 Claims, No Drawings

NON-IRRITATING INJECTABLE DOSAGE FORMS

This invention relates to injectable dosage forms. In one particular aspect, it relates to compositions and methods of administering without irritation injectable dosage forms of tissue irritating medicaments.

Certain medicaments, e.g., phenothiazines, upon injection cause tissue irritation at the injection site. It has been unexpectedly found that when these tissue irritating medicaments are formulated in glyceride vehicles, tissue irritation at the injection site is prevented.

Broadly, this invention provides a non-irritating injectable dosage form of a tissue irritating medicament, which comprises the tissue irritating medicament, e.g., thioridazine base in association with a pharmaceutically acceptable glyceride vehicle comprising a glycerol ester of a saturated or unsaturated fatty acid having from 6 to 20 carbon atoms, e.g., hexanoic acid, octanoic acid, decanoic acid, myristic acid, oleic acid, lauric acid, linoleic acid and the like, or mixtures thereof.

It is understood that the glyceride vehicle may include the mono-, di-, or triglyceryl ester of the fatty acid or mixed glycerides wherein at least one molecule of glycerol has been esterified with fatty acids or varying carbon atom length.

The glyceride vehicle of this invention is preferably a mixture of glycerides of saturated vegetable fatty acids having substantially a carbon chain length of about $C_8$ to about $C_{12}$. More preferably, the carbon chain length is from about $C_8$ to about $C_{10}$. The triglycerides are most preferred.

Examples of the glycerides with which this invention is concerned are the Miglyols ® (K. Fries Inc., Montvale, N.J.), sesame oil, corn oil, and cottonseed oil. The physical and chemical composition of Miglyols are shown in Table I.

Among the medicaments with which this invention is concerned are the phenothiazines, e.g., thioridazine, mesoridazine, chloropromazine, prochlorperazine, promethazine, trifluoroperazine, trimeprazine, thiethylperazine and the like.

When a suspension of the medicament base in the glyceride vehicles is prepared, the medicament is preferably reduced in particle size, e.g, micronized, to about 3 to about 100 microns for use with conventional hypodermic needles, e.g., 18 to 22 gauge needles.

EXAMPLE 1

To determine the effectiveness of the formulations of this invention in preventing tissue irritation, the following substances were injected into muscles of rabbits and the injection sites examined by macroscopic and microscopic means at 4, 7 and 14 days after injection:

(A) Mellaril ® Base[1] in Miglyol 812 vehicle at concentrations of 22.51 mg/ml ($A_1$);
  11.26 mg/ml ($A_2$); and 5.63 mg/ml ($A_3$).
[1]Free base form of thioridazine hydrochloride-Mellaril® Sandoz Pharmaceuticals, Inc.

(B) DiMellaril Pamoate in Miglyol 812 vehicle at concentrations of 22.4 mg/ml ($B_1$); 11.12 mg/ml ($B_2$); and 5.56 mg/ml ($B_3$).

(C) Sesami Oil 100%

(D) Miglyol 812 100%

(E) Sodium chloride Injectable[2]
[2]Sodium Chloride Injectable—Eli Lilly & Co.

METHOD

Forty-five (45) New Zealand white rabbits weighing approximately 5 to 8 lbs. were used. The animals had feed and water ad libitum and were observed daily.

The test formulations injected were 1 cc. in volume and injections were made with 3 cc. disposable syringes and 20 gage hypodermic needles. The injections were made within the thick back muscles (sacrospinales group) through closely shaven or clipped skin, swabbed with 70% alcohol.

All rabbits were injected on Day 0, with 13 rabbits sacrificed (using intraveneous sodium pentobarbital) on each of days 4, 7 and 14 after injection. The injection sites were randomized on the rabbits. Within each group of 15 rabbits, 6 injections were made for each of the A, and B concentrations, and 8 injections for the C,D and E concentrations.

DISSECTION AND EXAMINATION OF LESIONS AND TISSUE PROCESSING

TABLE 1

| | PHYSICAL CHARACTERISTICS | | | |
|---|---|---|---|---|
| | MIGLYOL 810 | MIGLYOL 812 | MIGLYOL 818 | MIGLYOL 840 |
| Acid value | 0.1 max | 0.1 max. | 0.2 max. | 0.1 max. |
| Saponification value | 340–360 | 325–345 | 315–320 | 320–340 |
| Iodine value | 1 max. | 1 max. | 10 max. | 1 max. |
| Unsaponifiable matter (%) | 0.3 max. | 0.3 max. | 0.2 max. | 0.3 max. |
| Iodine colour value | 2.0 max. | 2.0 max. | 3.1 max. | 2.0 max. |
| Cloud point | 0° C. max. | 10° C. max. | 10° C. max. | −10° C. max. |
| Moisture (%) | 0.15 max. | 0.15 max. | 0.15 max | 0.15 max. |
| Density at 20° C. | 0.94–0.96 | 0.94–0.96 | 0.93–0.95 | 0.92–0.94 |
| Refraction at 20° C. | 1.4490–1.4510 | 1.4480–1.4500 | 1.4490–1.4510 | 1.440–1.442 |
| Viscosity at 20° C. (cps.) | 27–30 | 28–32 | 30–33 | 9–12 |

| | DISTRIBUTION OF THE FATTY ACIDS IN THE GLYCERIDE | | | |
|---|---|---|---|---|
| Fatty Acids | MIGLYOL 810 | MIGLYOL 812 | MIGLYOL 818 | MIGLYOL 840 |
| Hexanoic acid ($C_6$) | 2% max. | 3% max. | 3% max. | 3% max. |
| Octanoic acid ($C_8$) | 65–75% | 50–65% | 45–60% | 65–80% |
| Decanoic acid ($C_{10}$) | 25–35% | 30–45% | 25–40% | 15–30% |
| Lauric acid ($C_{12}$) | 2% max. | 5% max. | 2–5% | 3% max. |
| Linoleic acid ($C_{18}$) | — | — | 3–6% | — |

The injectable dosage forms of this invention may be prepared in a conventional manner by dissolving or suspending the medicament base in the glyceride vehicle. Pharmaceutically acceptable preservatives and/or antioxidants may be added to the dosage form if desired.

After dissection (removal) of the sacrospinales muscles, the location of each injection site (unless apparent as a lesion) was identified and immersed in tubs of formalin for fixation.

After fixation, the lesions were dissected and measured in millimeters to calculate the lesion volume. Dimensions used were length, width and thickness.

The average volume of positive lesions were calculated by dividing the sum of the lesion volumes by the number of positive lesions.

When thorough dissection failed to reveal gross lesions, representative samples of muscle were collected in the regions of the injection site and processed for histologic review.

Samples of each lesion or injection site were embedded in paraffin, sectioned at 5 mm and stained with selected stains for microscopic examination.

HISTOLOGIC STAINING PROCEDURES

The following staining procedures[1] were used to demonstrate the components of the degree of the reaction to the injected materials.

[1]Thompson, S. W., "Selected Histochemical and Histopathological Methods", C. C. Thomas, 1966.

(1) Hematoxylin and Eosin (H&E): Used routinely for the initial evaluation of the injection site.

(2) Gomori's Trichome Stain: Used as needed to differentiate connective tissues from skeletal muscle fibers and to make more conspicuous injured skeletal muscle fibers, since the sarcoplasm undergoes alterations in tinctorial characteristics after injury.

To maintain objectivity, all slides were examined with complete lack of knowledge of specimen identity. Thus, substance, injected concentration and time were unknown.

RESULTS AND DISCUSSION

MACROSCOPIC OBSERVATIONS (Appearance and Lesion Volume) Intramuscular lesion volumes 4, 7 and 14 days post injection.

While considerable variation exists in determining the lesion volume at an injection site, it provides an approximate guide concerning the degree of lesion development.

The following Table 2 summarizes the relative lesion volumes resulting from the materials injected at the times specified:

TABLE 2

| Substance | Days 4 | | 7 | | 14 | |
|---|---|---|---|---|---|---|
| A1 | 3/6* | 91** | 0/6 | 0 | 0/6 | 0 |
| A2 | 0/6 | 0 | 0/6 | 0 | 0/6 | 0 |
| A3 | 2/6 | 55 | 0/6 | 0 | 0/6 | 0 |
| B1 | 6/6 | 2250 | 6/6 | 1406 | 6/6 | 238 |
| B2 | 5/6 | 1076 | 5/6 | 238 | 3/6 | 166 |
| B3 | 5/6 | 212 | 4/6 | 152 | 0/6 | 0 |
| C | 0/8 | 0 | 0/8 | 0 | 0/8 | 0 |
| D | 2/8 | 15 | 0/8 | 0 | 0/8 | 0 |
| E | 2/8 | 440 | 1/8 | 10 | 0/8 | 0 |

\* = # Positive Sites/# Sites Examined
\*\* = Volume in mm$^3$.

The lesion data from Table 2 shows an absence of significant lesions with the injection of Mellaril base in Miglyol, whereas the DiMellaril Base in Miglyol caused lesions which were conspicuous and regresed slowly with time. Little gross evidence of irritation was noted in response to injection of the Miglyol vehicle, Sesame Oil and Saline.

MICROSCOPIC OBSERVATION

There was the total absence of evidence of suppuration in response to Mellaril base in Miglyol at any of the times studies and at any of the concentrations injected.

No evidence of any suppuration was noted with the Miglyol, sesame oil or saline vehicle.

Myositis suppurative was characterized at days 4 and 7 in response to all concentrations of the DiMellaril Pamoate in Migloyl.

EXAMPLE 2

Following the procedure and method of Example 1, the following substances were tested for tissue irritation in 45 New Zealand white rabbits weighing approximately 5.25 to 9.5 lbs.

(F) Mellaril base in aqueous solution at 23.13 mg/ml (F1); 11.56 mg/ml (F2); and 5.7 mg/ml (F3).

(G) DiMellaril Pamoate in aqueous solution 22.78 mg/ml (G1); 11.39 mg/ml (G2); and 5.69 mg/ml (G3).

(H) Chlorpromazine base[3] in aqueous solution 25 mg/ml (H1); and 6.2 mg/ml (H2).

(I) Aqueous solution—vehicle.

(J) Sodium chloride—Saline.

[3]Thorazine-SKF

RESULTS AND DISCUSSION

MACROSCOPIC OBSERVATIONS (Appearance and Lesion Volume) Intramuscular lesion volumes, 4, 7 and 14 days post injection.

The following Table 3 shows the relative lesion volumes resulting from the materials injected at the times specified:

TABLE 3

| Substance | Day 4 | | 7 | | 14 | | |
|---|---|---|---|---|---|---|---|
| F1 | 100% | 6/6* | 3283** | 6/6 | 2666 | 6/6 | 3516 |
| F2 | 50% | 6/6 | 1117 | 1/5 | 100 | 4/6 | 1425 |
| F3 | 25% | 6/6 | 295 | 4/6 | 1200 | 5/6 | 170 |
| G1 | 100% | 6/6 | 1600 | 6/6 | 1333 | 5/6 | 184 |
| G2 | 50% | 6/6 | 1100 | 6/6 | 866 | 5/6 | 282 |
| G3 | 25% | 5/6 | 1080 | 6/6 | 586 | 6/6 | 190 |
| H1 | 100% | 6/6 | 5650 | 5/5 | 2820 | 6/6 | 2350 |
| H2 | 25% | 6/6 | 3616 | 5/5 | 1140 | 4/6 | 600 |
| I | 100% | 1/6 | 100 | 0/5 | 0 | 0/6 | 0 |
| J | 100% | 0/6 | 0 | 0/6 | 0 | 0/6 | 0 |

*Gross Lesion frequency (#positive/#examined) - 6 sites examined at time specified.
**Lesion Volume (mm3) at time specified
***It does not include lesion volume data from animal 625-77 which died on Day 1.

RESULTS AND DISCUSSION

MACROSCOPIC OBSERVATIONS (Appearance and Lesion Volume)

Lesions were produced at virtually all sites injected with the Mellaril base in aqueous solution.

The lesion volumes arising from the $F_1$, $F_2$, and $F_3$ concentrations of Mellaril base in aqueous solution showed little apparant change in size during the 4,7 and 14 day observation periods.

The DiMellaril Pamoate induced lesions at $G_1$, $G_2$ and $G_3$ concentration. It produced a slightly different pattern from the Mellaril Base in that the lesion volume size for the $G_1$ remained constant for Days 4 and 7, however, dropped considerably in size by Day 14. The same situation was seen at $G_2$ and it appeared that $G_3$ the lesion volume size had diminished by Day 7 and further by Day 14.

The $H_1$ chlorpromazine injections showed a decrease in relative size gradually from the largest noted at Day 4. By Days 7 and 14 the volume dropped to about half that seen at Day 4. In the $H_2$ concentration the lesion volume drop off in size followed the same pattern diminishing substantially by Day 14.

A barely perceptible lesion was seen at day four at one Aqueous vehicle site. No lesions were seen in response to injection of Sodium Chloride.

MICROSCOPIC OBSERVATIONS

Regardless of the concentration injected, there appeared to be a high-frequency evidence of suppuration in the inflammatory zone at Day 4 post-injection in response to the Mellaril base. There was no evidence of suppuration with the aqueous vehicle.

In response to the Mellaril base, the DiMellaril Pamoate and the chloropromazine evidence of connective tissue irritation became apparent by Day 7 and more frequent and extreme in its occurrence by Day 14 as one would expect. There appeared to be no real difference between the frequency of occurrence of connective tissue irritation as it related to time and dosage in the relationship to the compound.

EXAMPLE 3

Following the procedure and method of Example 1, the following substances were injected into muscles of rabbits and the injection sites examined by macroscopic means at 7 days after injection:

(K) Thioridazine Base in Sesame oil U.S.P.
(L) Thioridazine Base in Corn oil U.S.P.
(M) Thioridazine Base in Cottonseed oil U.S.P.
(N) Chlorpromazine Base in Miglyol 813 Vehicle
(O) Chlorpromazine Base in Sesame oil U.S.P.
(P) Thiethylperazine Base in Miglyol 812 Vehicle
(Q) Thiethylperazine Base in Sesame oil U.S.P.
(R) Thiethylperazine Base in Cottonseed oil U.S.P.
(S) Thiethylparazine Maleate in Aqueous Vehicle.

All the substances were injected at dose equivalents of 25 mg/ml.

Method

Four (4) New Zealand white rabbits weighing approximately 5 to 8 lbs. were used. The animals had feed and water ad libitum and were observed daily.

The test formulations injected were 1 cc. in volume and injections were made with 3 cc. disposable syringes and 20 gauge hypodermic needles. The injections were made within the thick back muscles (sacrospinales group) through closely shaven or clipped skin, swabbed with 70% alcohol.

All rabbits were injected on Day 0, with the rabbits sacrificed (using intraveneous sodium pentobarbital) at 7 days after injection. The injection sites were randomized on the rabbits.

After dissection (removal) of the sacrospinales muscles, the location of each injection site (unless apparent as a lesion) was identified and immersed in tubs of formalin for fixation.

After fixation, the lesions were dissected and measured in millimeters to calculate the lesion volume. Dimensions used were length, width and thickness.

The following Table 4 summarizes the lesion volume resulting from the materials injected at the end of 7 days:

TABLE 4

| Substance | Day 7 | Substance | Day 7 |
|---|---|---|---|
| K | 0* | P | 0 |
| L | 0.004** | Q | 0.02** |
| M | 0 | R | 0 |
| N | 0 | S | 0.8 |
| O | 0 | | |

\* = Volume in mm$^3$.
\*\* = Insignificant.

The results of Examples 1, 2 and 3 show the novel and unobvious result from the use of glyceride vehicles of this invention with the base form of a tissue irritating medicament in preventing the irritation of tissue at an injection site.

What is claimed is:

1. Method of administering without irritation an injectable dosage form of a tissue irritating medicament, which comprises administering to a patient in need of the medicament, a therapeutically effective amount of thioridazine, in base form in association with a sufficient amount of a pharmaceutically acceptable glyceride vehicle comprising a glycerol ester of a saturated or unsaturated fatty acid which fatty acid has from 6 to 20 carbon atoms or mixtures thereof to form an injectable dosage form.

2. The method according to claim 1 wherein the glyceride vehicle is sesame oil, corn oil or cottonseed oil.

3. The method according to claim 1 wherein the glyceride vehicle is a glycerol ester comprising a saturated vegetable fatty acid having substantially from 8 to 12 carbon atoms or mixtures thereof.

4. The method according to claim 1 wherein the glyceride vehicle has a fatty acid composition to about 3% hexanoic acid, from about 50 to 65% octanoic acid, from about 30 to about 45% decanoic acid and to about 5% lauric acid based on the weight of the glyceride.

5. Method of administering without irritation an injectable dosage form of a tissue irritating medicament, which comprises administering to a patient in need of the medicament, a therapeutically effective amount of thioridazine, in base form in association with a sufficient amount of pharmaceutically acceptable sesame oil.

6. A non-irritating injectable dosage form of a tissue irritating medicament, which comprises a therapeutically effective amount of thioridazine, in base form in association with a sufficient amount of a pharmaceutically acceptable glyceride vehicle comprising a glycerol ester of a saturated or unsaturated fatty acid which fatty acid has from 6 to 20 carbon atoms or mixtures thereof to form the injectable dosage form.

7. The injectable dosage form according to claim 6 wherein the glyceride vehicle is sesame oil, corn oil, or cottonseed oil.

8. The injectable dosage form according to claim 6 wherein the glyceride vehicle is a glycerol ester comprising a saturated vegetable fatty acid having substantially from 8 to 12 carbon atoms or mixtures thereof.

9. The injectable dosage form according to claim 6 wherein the glyceride vehicle has a fatty acid composition to about 3% hexanoic acid, from about 50 to 65% octanoic acid, from about 30 to 45% decanoic acid and to about 5% lauric acid based on the weight of the glyceride.

10. A non-irritating injectable dosage form of a tissue irritating medicament, which comprises a therapeutically effective amount of thioridazine, in base form in association with a sufficient amount of pharmaceutically acceptable sesame oil.

\* \* \* \* \*